US010702562B2

(12) United States Patent
O'Neill et al.

(10) Patent No.: US 10,702,562 B2
(45) Date of Patent: Jul. 7, 2020

(54) ANTI-BACTERIAL LYSATE OF PROBIOTIC BACTERIA

(71) Applicant: SKINBIOTHERAPEUTICS PLC, Macclesfield (GB)

(72) Inventors: Catherine O'Neill, Manchester (GB); Andrew McBain, Manchester (GB)

(73) Assignee: Skinbiotherapeutics PLC, MacClesfield (GB)

( * ) Notice: Subject to any disclaimer, the term of this patent is extended or adjusted under 35 U.S.C. 154(b) by 39 days.

(21) Appl. No.: 15/314,897

(22) PCT Filed: May 26, 2015

(86) PCT No.: PCT/GB2015/051529
§ 371 (c)(1),
(2) Date: Nov. 29, 2016

(87) PCT Pub. No.: WO2015/181534
PCT Pub. Date: Dec. 3, 2015

(65) Prior Publication Data
US 2017/0196919 A1    Jul. 13, 2017

(30) Foreign Application Priority Data

May 29, 2014  (GB) .................................. 1409541.8

(51) Int. Cl.
| | | |
|---|---|---|
| A61K 35/747 | (2015.01) | |
| A61K 9/00 | (2006.01) | |
| A61K 35/74 | (2015.01) | |
| A61K 35/00 | (2006.01) | |

(52) U.S. Cl.
CPC .......... *A61K 35/747* (2013.01); *A61K 9/0014* (2013.01); *A61K 35/74* (2013.01); *A61K 2035/11* (2013.01)

(58) Field of Classification Search
None
See application file for complete search history.

(56) References Cited

U.S. PATENT DOCUMENTS

| 7,651,680 B2 * | 1/2010 | Breton ...................... A61K 8/19 424/600 |
| 2011/0039765 A1 * | 2/2011 | Connor ...................... C07K 1/20 514/3.8 |

FOREIGN PATENT DOCUMENTS

| WO | 2009155711 A1 | 12/2009 |
| WO | 2013153358 A1 | 10/2013 |
| WO | 2015181534 A1 | 12/2015 |

OTHER PUBLICATIONS

Lu et a., Journal of Pediatric Gastroenterology and Nutrition, vol. 49:23-30, 2009.*
Wang et al., Am J Physiol Gastrointest Liver Physiol. Jul. 1, 2012; 303(1): G32-G41, pp. 1-23.*
Augustin et al., International Journal of Engineering Research and Applications, vol. 2, Issue 5, 2012, pp. 974-985.*
Lu et al., J. of Pediatric Gastroenterology and Nutrition, Journal of Pediatric Gastroenterology and Nutrition, vol. 49, pp. 23-30, 2009.*
Vanlerbergue Master's Thesis, University of Ghent, 2009.*
International Search Report and Written Opinion for PCT/GB2015/051529 dated Jul. 17, 2015.
De Keersmaecker et al., "Strongantimicrobial activityofLactobacillus rhamnosus GG against *Salmonella typhimurium* is due to accumulation of lactic acid." FEMS Microbiol Lett, vol. 259, 2006, pp. 89-96.
Doron et al., "Pribiotics: their role in the treatment and prevention of disease." Expert Rev. Anti Infect. Ther, vol. 4, No. 2, 2006, pp. 261-275.
Lu et al., "M1208 Six Small Bioactive Peptides Identified from Lactobacillus GG Cultured Supernatant." Gastroenterology, vol. 134, No. 4, Apr. 2008, AGA Abstracts, p. A-361.

* cited by examiner

*Primary Examiner* — David W Berke-Schlessel
(74) *Attorney, Agent, or Firm* — Denise L. Mayfield; Dykema Gossett PLLC

(57) ABSTRACT

The invention relates to probiotic bacteria and particularly, although not exclusively, to anti-bacterial compositions derived from probiotic bacteria. Disclosed are compositions comprising material secreted from probiotic bacteria, uses thereof, and methods using the compositions. Particularly contemplated are compositions comprising material secreted from *Lactobacillus rhamnosus*, and uses thereof.

20 Claims, 6 Drawing Sheets

ANTI-BACTERIAL LYSATE OF PROBIOTIC BACTERIA

FIELD OF THE INVENTION

The present invention relates to probiotic bacteria and particularly, although not exclusively, to anti-bacterial compositions derived from probiotic bacteria.

BACKGROUND TO THE INVENTION

The concept that probiotics are beneficial to gut health has been investigated for a number of years. Studies have demonstrated that probiotics potentially improve gut function through a number of mechanisms including increasing epithelial barrier function (40) and modulation of the immune response (6, 51). There is also evidence that probiotics can prevent colonisation of the gut by pathogens. This can be via mechanisms such as down regulation of virulence factors and inhibition of pathogen adherence to the epithelium (2). For example, lactobacillus species inhibit the adhesion of *Enterobacter sakazakii* to intestinal mucus by competitive exclusion (32). Other studies demonstrated that some probiotics increase the production of intestinal mucin thus inhibiting pathogen adherence to intestinal epithelial cells (31). Probiotics are also able to produce antimicrobial peptides (bacteriocins) and acids. Collectively, there are numerous probiotic mediated mechanisms that limit pathogen colonisation (33).

Since probiotics may have positive impacts on the gut, their potential effects on other systems, such as the mouth (18) and the urogenital tract (44) have also begun to be investigated. A study in 2001, examining the impact of oral administration of Lactobacilli in a clinical trial of women with bacterial vaginosis, showed that Lactobacilli could indeed inhibit the colonization of uro-epithelial cells by pathogens (44). Recently, the topical application of probiotics to the skin has been investigated in a limited number of studies. Topical application of sonicated *Streptococcus salivarius* strains to patients suffering from atopic dermatitis resulted in improved barrier function apparently through increasing the level of ceramides in the stratum corneum (13). Topically applied *L. plantarum* for treatment of infected wounds resulted in improved tissue repair in a mouse burn model and prevention of infection in chronic leg ulcers and burns in humans (41, 42). However, in general the mechanisms underlying these effects are not well understood.

*Staphylococcus aureus* is both a transient coloniser of skin and a major opportunistic skin pathogen, causing diseases ranging from impetigo to life threatening conditions such as sepsis (25). Previously, our lab demonstrated that the probiotic *L. reuteri* could protect epidermal keratinocytes from the toxic effects of *S. aureus* via competitive exclusion of the pathogen from keratinocyte binding sites (43). The inventors have now identified *L. rhamnosus* GG as a second probiotic with the ability to protect skin cells from the effects of *S. aureus*. However, *L. rhamnosus* GG uses multiple mechanisms to protect against infection including inhibition of *S. aureus* growth, competitive exclusion and displacement of the pathogen from keratinocytes.

SUMMARY OF THE INVENTION

Few studies have evaluated the potential benefits of the topical application of probiotic bacteria or material derived from them. The inventors have investigated whether a probiotic bacterium, *Lactobacillus rhamnosus* GG can inhibit *Staphylococcus aureus* infection of human primary keratinocytes in culture. When primary human keratinocytes were exposed to *S. aureus*, only 25% of the keratinocytes remained viable at 24 h afterwards. However, in the presence of $10^8$ CFU/ml of live *L. rhamnosus* GG, the viability of the infected keratinocytes increased to 57% (P=0.01). Interestingly, *L. rhamnosus* GG lysates and spent culture fluid also provided significant protection to keratinocytes with 65% (P=0.006), and 57% (P=0.01) of cells respectively, being viable following 24 h incubation. Keratinocyte survival was significantly enhanced regardless of whether the probiotic was applied in viable form, or as lysates, 2 h before or simultaneously (P=0.005) or 12 h after (P=0.01) *S. aureus* infection. However, spent culture fluid was only protective if added before or simultaneously to *S. aureus*. With respect to mechanism, both *L. rhamnosus* GG lysate or spent culture fluid apparently inhibited adherence of *S. aureus* to keratinocytes by competitive exclusion but, only viable bacteria or the lysate could displace *S. aureus* (P=0.04 and 0.01, respectively). Furthermore, growth of *S. aureus* was inhibited by either live bacteria or lysate but not spent culture fluid. Together, these data suggest at least two separate activities involved in the protective effects of *L. rhamnosus* GG against *S. aureus*, growth inhibition and reduction of bacterial adhesion.

The inventors have previously demonstrated that probiotic bacteria and lysates thereof in protecting cells against infection by pathogenic bacteria such as *S. aureus* (see WO2013/153358). They have now demonstrated that cell free culture supernatant, in which the probiotic bacteria have previously been cultured, is also capable of preventing pathogenic bacteria adhering to, or infecting, cells. Thus, probiotic bacteria are able to protect cells from infection by at least two mechanisms. Firstly, the probiotic bacteria may be able to reduce or inhibit the growth of pathogenic bacteria through one or more agents contained within the probiotic bacterium that are able to directly inhibit growth and/or viability of the pathogenic bacteria. Secondly, and as identified herein, one or more agents that are secreted from the probiotic bacteria (and thus present in the culture media) are able to inhibit the ability of the pathogenic bacteria to infect the cells, possibly through preventing adhesion of the pathogenic bacteria to the cells. Material secreted by the probiotic bacteria is therefore protective against pathogenic bacterial infection. Thus, the secreted material has anti-bacterial, or anti-infective properties that can be harnessed in a variety of anti-bacterial compositions as described here.

DESCRIPTION

The invention includes the combination of the aspects and preferred features described except where such a combination is clearly impermissible or expressly avoided.

The section headings used herein are for organizational purposes only and are not to be construed as limiting the subject matter described.

Probiotic Bacteria

The invention relates to the use of probiotic bacteria. Probiotics are commonly defined as "live microorganisms which when administered in adequate amounts confer a health benefit on the host". Studies in the gut have demonstrated the ability of probiotic bacteria to inhibit colonisation by pathogens through mechanisms including exclusion, competition and displacement of pathogen attachment to the host tissues. As used herein, the term "probiotic bacterium"

may also refer to such bacteria when they are no longer alive, for example following inactivation by heat or radiation.

*Lactobacillus rhamnosus*

The invention particularly relates to probiotic bacteria of the species *Lactobacillus rhamnosus*. Such bacteria were originally considered a subspecies of *Lactobacillus casei*, but later genetic research found it to be a species of its own. A number of *L. rhamnosus* strains are known. For example, strains 1-1720 (Pasteur collection Nationale de Cultures de Microorganismes), AC413, GR-1 (Karlsson et al., BMC microbiology 2012, 12:15), JB-1 (Bravo et al., PNAS 2011 108(38) 16050-16055) GG and LC705 (Savijok et al., J. Proteome Research 2011 10(8) 3460-3474). Other strains of *L. rhamnosus* may be readily isolated.

In particular, the invention relates to *L. rhamnosus* GG. *L. rhamnosus* GG (also referred to herein as LGG) is deposited at ATCC (American Tissue Culture Collection) under accession number ATCC 53103. BGG was isolated in 1983 from the intestinal tract of a healthy human being by Gorbach and Goldin.

Compositions

The compositions according to the invention comprise or consist of secreted material from probiotic bacteria.

Secreted material refers to material secreted from a probiotic bacterium. The secreted material may be a single agent. It may be a mixture of more than one agent. The secreted material may include proteins, carbohydrates, nucleic acids or lipids. Secreted material may include the secretome, which is all of the secreted proteins and secretory machinery of the probiotic bacterium. It may additionally encompass molecules that are not proteins, such as carbohydrates, lipids and nucleic acid.

Some compositions described herein contain secreted material in a carrier. The carrier is usually a solution in which the secreted material is dissolved, suspended, diluted or admixed.

In some cases the carrier may be the medium which has been in contact with the probiotic bacterium during culturing. The composition of the medium will have changed during the culture, for example by the secretion of material from the probiotic bacterium. The compositions may consist or comprise culture medium in which the probiotic bacteria have been growing in.

Media suitable for culturing probiotic bacteria is well known to those of skill in the art. As used herein the terms "media" and "medium" encompasses any nutrient containing liquid in which microorganisms such as bacteria may be supported, kept alive, grown and/or expanded. The media may contain the minimal nutrients to support bacterial life, and optionally other nutrients. Exemplary nutrients contained within the broth include sugar, magnesium, phosphate, phosphorous and sulphur. The media may be made to, or modified from, a combination of nutrients that is well known in the art, such as Wilkins-Chalgren Broth. Media may be obtained pre-mixed from a commercial source, or may be made in-house.

The probiotic bacterium may have been in contact with the media for at least six hours, at least twelve hours, at least eighteen hours, at least twenty four hours, at least 3 days, at least 4 days, at least 5 days, at least 6 days, at least 7 days, at least 8 days, at least 9 days, at least 10 days, at least two weeks or longer.

The probiotic bacteria may have been cultured in the media, or in contact with the media, under aerobic or anaerobic conditions. Preferably the probiotic bacteria have been cultured under anaerobic conditions. For example, the culture may be performed under 10% $H_2$, 10% $CO_2$, 80% $N_2$.

The probiotic bacteria may have been cultured in the media under conditions that facilitate growth and expansion of the probiotic bacteria. Such conditions are well known to those of skill in the art. For example, the culture may be incubated at 37° C.

Preferably the composition does not contain any probiotic bacteria. The probiotic bacteria may have been removed from the media, for example by centrifugation and/or filtration. For example, the bacteria may be removed by sedimenting them from the media in a centrifuge at 15,000×g for a period of time sufficient for substantially all of the bacteria to sediment from the media. The media may be filtered using a microporous filter with pores of a suitable size to remove substantially all of the bacteria from the media. These methods may remove intact bacteria, and may also remove bacterial debris, such as the remains of any bacteria that have undergone cell lysis such as by apoptosis. The media containing secreted material has not been obtained from a culture that has undergone a lysis process, and thus is not, and has not been obtained from, a lysate.

The composition may be sterile. That is to say that the secreted material has been subject to a sterilisation process, such as irradiation, heat, chemicals, pressure or filtration, or any combination thereof. This may include autoclaving, x-ray sterilization or UV-light sterilisation. In the case of media containing the secreted material, the media may have been sterilised before the probiotic bacteria were introduced and cultured, and also after the bacteria had been removed from that media.

In some cases the composition comprising secreted material contains substantially no intact bacteria. The composition may also be substantially free from lysed bacteria or bacterial fragments, such as bacteria that have undergone apoptosis. The intact bacteria and/or lysed bacteria or bacterial fragments may have been separated from the secreted material. Separation may occur by any suitable means known in the art, such as centrifugation or filtration. By "substantially free from" we mean that the secreted material contains no or minimal contamination of non-secreted bacterial components, such as whole bacteria, lysed bacteria, or bacterial fragments. Thus, the composition may contain 100% secreted material, at least 99% secreted material, at least 95% secreted material, at least 90% secreted material, at least 85% secreted material, at least 80% secreted material, at least 75% secreted material or at least 70% secreted material. The secreted material may comprise additional components of non-bacterial origin, such as carrier solutions, other active agents, or preservatives, as described herein.

Compositions as described herein may be prepared by culturing a probiotic bacteria in media, separating the probiotic bacteria from the media, and preparing a composition from the media. The probiotic bacteria may be cultured under anaerobic conditions. The probiotic bacteria may be cultured at a temperature above the normal temperature of the human body. The probiotic bacteria may be cultured at 30° C., 31° C., 32° C., 33° C., 34° C., 35° C., 36° C., 37° C., 38° C., 39° C., 40° C. or 41° C. Preferably the probiotic bacteria are cultured at 37° C. The probiotic bacteria may be cultured in the media for 1 day, 2 days, 3 days, 4 days, 5 days, 6 days, 7 days, 8 days, 9 days, 10 days, 11 days, 12 days, 13 days or 14 days. The probiotic bacteria or lysed bacteria or fragments of bacteria may be separated from the media by centrifugation, such as centrifugation at 15000×g.

The media may be separated from the probiotic bacteria, lysed bacteria or fragments of bacteria by filtration. The media may be separated by a combination of filtration and centrifugation. The media may be subject to sterilisation, before or after the probiotic bacteria are removed. For example, following separation of the media from the whole bacteria, lysed bacteria or bacterial fragments, the media may be subject to sterilisation. The media may be subject to concentration, such that the proportion of secreted material increases relative to the total volume of media. Concentration may occur by any method known in the art, such as evaporation. Secreted material may be separated from the media. Any method of separating material from a carrier solution may be used. For example the secreted material may be separated from the media by chromatography, crystallisation, distillation, drying, electrophoresis or precipitation. Once isolated from the media, or concentrated in the media, the secreted material may be dissolved or diluted in a carrier, or otherwise formulated into a composition as disclosed herein.

Therapeutic Applications

The compounds and compositions of the present invention are useful in the treatment of a wide range of diseases and conditions. In particular they are useful in the treatment and prevention of skin infections, including bacterial infections. In particular, the compounds and compositions are useful in the treatment or prevention of *S. aureus* infections. The compounds and compositions are particularly useful in the treatment of soft tissue bacterial infections, such as skin infections. The compounds and compositions of the present invention are particularly useful in the prevention or treatment of *S. aureus* skin infections.

The invention relates to the prevention or treatment of infections. The probiotic compositions of the present invention exhibit anti-infection activity. For example, anti-adhesion activity, including preventing the adhesion of *S. aureus* to cells. Thus, the compositions are useful for the prevention or treatment of infections including bacterial infections, such as the prevention or treatment of multi-drug resistant bacterial infections, hospital acquired bacterial infections, antibiotic resistant bacterial infections, infections by gram negative and/or gram positive bacterial infections.

The compositions of the invention are useful in the prevention of infections by *Staphylococcus* spp., such as *S. saprophyticus, S. xylosus, S. lugdenensis, S. schleiferi, S. caprae, S. epidermidis, S. saprophyticus, S. wameri, S. aureus, S. hominis*, Methicilin resistant *S. aureus* (MRSA), *S. pyrogenes, S. salivariu, S. mutans* and *S. pneumonia*.

In particular the compositions of the invention exhibit anti-*Staphylococcus* adhesion activity, and are therefore useful in the prevention or treatment of *Staphylococcus* infection. For example, the compositions of the invention exhibit anti-*Staphylococcus aureus* activity, and are therefore useful in the prevention or treatment of *S. aureus* infections.

Infections occur where disease causing microorganisms invade the tissues of the body. Multiplication of those microorganisms and the toxins that they produce react with the tissues of the body, often causing immune reactions by the infected host. Infections may be caused by bacteria, viruses, viroids, fungi and other parasites. Infections may occur via any of the tissues of the body, such as the skin, gut or membranes. In some embodiments of the invention the probiotic bacteria or lysates of the invention are used to treat infection of tissues other than the gut, for example in some embodiments the probiotic bacterium or lysate according to the invention is not used for the treatment of infection of the alimentary canal, esophagus, stomach, intestines, rectum or anus. In particular aspects the invention relates to the treatment or prevention of infection of the external surface of the body, and particularly the skin.

The compositions according to the invention may be used in the prevention or treatment of skin infections. The infection may be due to a bacterium, such as a *Staphylococcus* bacteria, including *S. aureus*. The composition may be applied separately, sequentially or simultaneously with exposure to the infective agent. Preferably, the composition is applied before exposure to the infective agent.

The compositions of the invention are preferably used for the prevention of bacterial infection. They are preferentially administered to a subject before that subject is exposed to the infective agent, such as *S. aureus*. The subject may have been identified as being at risk of infection by the infective agent. Subjects may be identified as being at risk of infection by an infective agent because of their environment, for example being situated in an environment where the inventive agent is known to exist, or due to the health of the subject, such as the existence of an open wound or poor immune health. For example, the compositions may be used in a hospital or other clinical environment in which a pathological bacteria is known to, or suspected to, be present.

In some cases, the patient is about to undergo, or has recently undergone, surgery. The compositions described herein may be used to prevent infection of an open wound such as a surgical incision or graft by a pathogenic bacteria.

In some cases the subject is determined not to have an infection by the infective agent. For example, the subject may be determined not to have a *S. aureus* infection. Methods for determining whether a subject has an infection are well known in the art, and may include the analysis of a sample obtained from the subject for the presence of the infective agent.

A composition may be administered alone or in combination with other treatments, either simultaneously or sequentially dependent upon the condition to be treated.

The secreted material may be dissolved in, suspended in, or admixed with one or more other pharmaceutically acceptable ingredients. The probiotic bacterium or lysate thereof may be presented in a liposome or other microparticulate.

In some embodiments, the secreted material may be provided as a suspension in a pharmaceutically acceptable excipient, diluent or carrier. In some embodiments probiotic bacterium may be provided as a lyophilisate.

Non Therapeutic Applications

The invention also provides antibacterial compositions in the form of cleaning products, washes, surface coatings or other compositions which are not for medical treatment of the human or animal body.

Such agents may be useful for removing, killing, or preventing the accumulation of bacteria on a surface, or inhibiting the action or growth of the bacteria. The secreted material is formulated as an antibacterial composition.

Anti-bacterial compositions according to the invention may be useful for treating biomaterials, implants and prosthesis (including stents, valves, eyes, hearing aids, gastric bands, dentures, artificial joint replacements etc), surgical instruments or other medical devices prior to administration to, or treatment of, or use with, a patient or subject. The antibacterial compositions may be useful for treating surfaces prone to colonisation or exposure to bacterial, such as handrails, food preparation surfaces, kitchen surfaces or equipment, tables, sinks, toilets or other bathroom hardware, Antibacterial compositions may comprise agents in addition to the lysate, such as cleaning agents, stabilisers, anionic surfactants, perfumes, chelating agents, acids, alkalis, buffers or detergents. Such agents may facilitate or enhance the antibacterial properties of the agent, such as killing or inhibiting bacteria, or preventing the recolonisation of the cleaned surface.

The present invention also gives rise to a method of preparing a surface comprising applying secreted material to the surface. The method may result in reduced colonisation of the surface by pathogenic microorganisms.

Fomulations

Whilst it is possible for the secreted material to be used alone, it is preferable to present it as a formulation comprising the material and a carrier. The secreted material may be dissolved in, suspended in, or admixed with one or more other ingredients. In some cases the secreted material is presented in a liposome or other microparticulate.

Formulations disclosed herein include skin care, wound care, respiratory care and oral care formulations, including medical, personal care and consumer products.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more active compounds and optionally one or more other pharmaceutically acceptable ingredients, including, for example, penetration, permeation, and absorption enhancers. Formulations may also suitably be provided in the form of a depot or reservoir.

In some formulations, the secreted material is formulated with one or more pharmaceutically acceptable ingredients. Pharmaceutically acceptable ingredients are well known to those skilled in the art, and include, but are not limited to, pharmaceutically acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Certain products and formulations herein are suitable for skin care or wound care. "Skin care" means topical personal care and/or health care products including products useful for the treatment of adult or infant skin to maintain or improve the health of the skin or improve the appearance of the skin. "Wound care" includes products for the treatment of a wound to assist in the closure or healing of the wound, and/or to reduce the pain or scarring associated with the wound, maintaining or improving the health of such tissue or skin, repairing such tissue or skin, and reducing irritation, itching and/or redness of such tissue or skin.

In some embodiments the secreted material according to the invention is formulated for topical administration, particularly for use or application to, or on, the skin.

Formulations suitable for topical administration include gels, pastes, ointments, creams, lotions, and oils, as well as patches, adhesive plasters, bandages, dressings, depots, cements, glues, and reservoirs.

Ointments are typically prepared from the secreted material and a paraffinic or a water-miscible ointment base.

Creams are typically prepared from the probiotic bacterium or lysate and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

Emulsions are typically prepared from the probiotic bacterium or lysate and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Some products and formulations described herein are suitable for oral care. "Oral care" means products for use and/or uses of materials in the oral cavity or any portion thereof, including products for use on the teeth, mucosa, tongue, and the like. Products and uses in the field of oral care include those intended for tooth aesthetics including, for example, tooth whitening, stain prevention, and the like, as well as anti-plaque, anti-gingivitis, anti-sensitivity, anti-caries, breath freshening, dry mouth relief, erosion repair and prevention, active delivery and retention, sensory enhancement and mouth feel alteration, and the like.

Formulations for oral care include dental sprays, mouthwashes, toothpastes, lozenges, antibacterial washes, drinks (e.g. milk, yoghurt), food items (such as yoghurt, ice cream, candy bars), or powdered foods (such as powdered milk). Formulations suitable for oral care include formulations suitable for oral and/or buccal administration.

Formulations suitable for oral administration (e.g, by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the active compound in a flavored basis, usually sucrose and acacia or tragacanth. Pastilles typically comprise the active compound in an inert matrix, such as gelatin and glycerin, or sucrose and acacia. Mouthwashes typically comprise the active compound in a suitable liquid carrier.

Some formulations disclosed herein are suitably provided as a patch, adhesive plaster, bandage, dressing, or the like which is impregnated with, or coated with, one or more secreted material according to the invention and optionally one or more other pharmaceutically acceptable ingredients, including, for example, penetration, permeation, and absorption enhancers. The probiotic bacteria, lysates or culture media may also be provided in the form of coatings for medical devices such as implants, prosthetics, surgical instruments, gloves, catheters, valves, pacemakers and the like.

Some compositions and formulations disclosed herein are suitable for respiratory care. "Respiratory care" means products for the treatment of conditions including prevention and treatment of rhinitis, sinusitis, seasonal allergies, nasal congestion and colds. The compositions may be useful for preventing a bacterial infection of the respiratory tract, including the sinuses, airways, throat or lungs. In some cases such formulations are formulated for intranasal administration or pulmonary administration.

Formulations suitable for intranasal administration, where the carrier is a liquid, include, for example, nasal spray, nasal drops, or by aerosol administration by nebuliser, include aqueous or oily solutions of the active compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Compositions and formulations according to the invention may further comprise other active agents, for example other anti-bacterial agents such as bactericidal agents.

In some embodiments a formulation for use according to the present invention may comprise at least about 0.01%, about 0.05%, about 0.1%, about 0.2%, about 0.3%, about 0.4%, about 0.5%, about 0.6%, about 0.7%, about 0.8%, about 0.9%, about 1.0%, about 1.5%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 20.0%, about 25.0%, about 30.0%, about 35.0%, about 40.0%, about 45.0%, about 50.0% by weight of secreted material.

In some embodiments the formulation may comprise, one of at least about 0.01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to 10 about 5%, by weight of secreted material.

Pharmaceutical Preparations

The probiotic preparations according to the invention may be formulated as pharmaceutical compositions for clinical use and may comprise a pharmaceutically acceptable carrier, diluent or adjuvant. They may be formulated for topical administration.

Administration is preferably in a prophylactically or therapeutically effective amount, this being an amount sufficient to show benefit to the individual. The actual amount administered, and rate and time-course of administration will depend on the nature and severity of the disease being treated. Prescription of treatment, e.g. decisions on dosage etc., is within the responsibility of general practitioners and other medical doctors, and typically takes account of the disorder to be treated or prevented, the condition of the individual patient, the site of delivery, the method of administration and other factors known to practitioners. Examples of the techniques and protocols mentioned above can be found in Remington's Pharmaceutical Sciences, 20$^{th}$ Edition, 2000, pub. Lippincott, Williams & Wilkins. It will be appreciated by one of skill in the art that appropriate dosages of the active compounds and compositions comprising the active compounds can vary from patient to patient.

The compositions of the present invention may be formulated as medicaments, that is to say formulated as a medicine. The medicament may include other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilisers, solubilisers, surfactants (e.g. wetting agents), masking agents, colouring agents, flavouring agents, and sweetening agents. The formulation may further comprise other active agents, for example other therapeutic or prophylactic agents.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which.

EXAMPLES

Example 1

Materials and Methods

Mammalian Cell Culture

Figure 1:
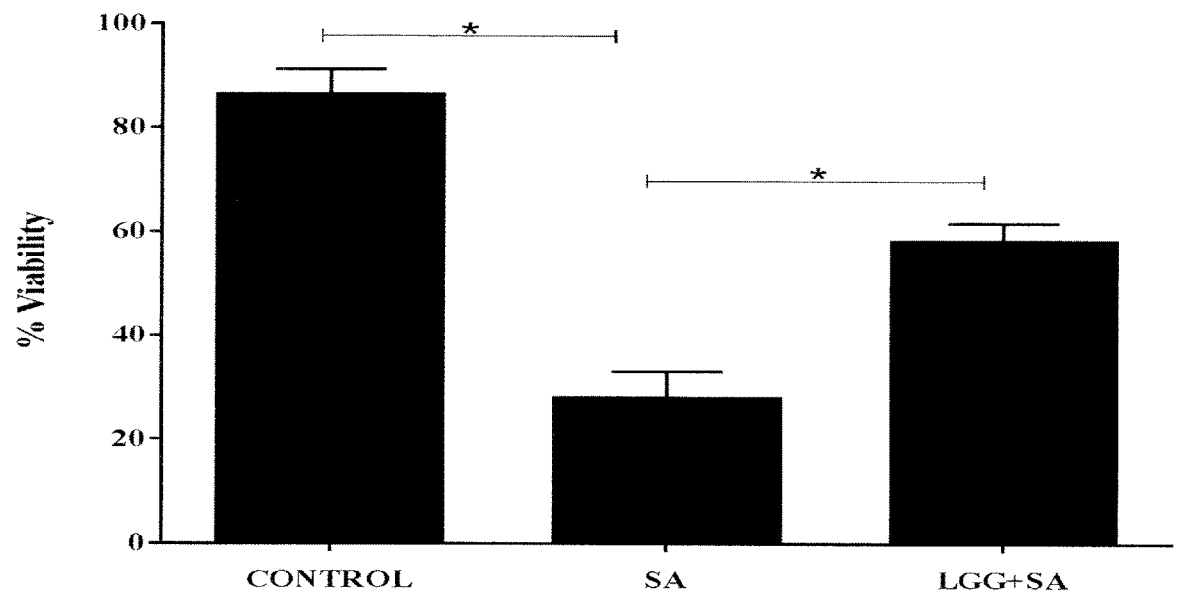
FIG. 1: *L. rhamnosus* GG protects keratinocytes from the toxic effects of *S. aureus*. Uninfected cells had a mean viability of (90%). *S. aureus* infected cells had a mean viability of (25%±3.4). In keratinocytes infected with a combination of *S. aureus* and *L. rhamnosus* GG (LGG+SA), the viability after 24 hours was 57%±2.7 (P=0.01, n=3).

Normal human epidermal keratinocytes (NHEK) cultured in keratinocyte basal medium (Promocell, Heidelberg, Germany) containing a supplement mix (bovine pituitary extract 0.004 mg/ml, epidermal growth factor (recombinant human) 0.125 ng/ml, insulin (recombinant human) 5 µg/ml, hydrocortisone 0.33 µg/ml, epinephrine 0.39 µg/ml and transferrin, holo (human) 10 µg/ml) and 0.06 mM $CaCl_2$ (Promocell, Heidelberg, Germany), were used as a model system. These were cultured routinely at 37° C. in a humid atmosphere of 5% $CO_2$ in T-75 culture flasks as described previously (43).

Bacterial Cell Culture

*Lactobacillus rhamnosus* Goldin and Gorbach (*L. rhamnosus* GG) (ATCC 53103, ATCC, Middlesex, UK) was grown routinely in Wilkins-Chalgren Broth or Agar (Oxoid, Basingstoke, UK) at 37° C. in incubated in an anaerobic cabinet (atmosphere, 10:10:80, $H_2$—$CO_2$—$N_2$). *Staphylococcus aureus* was grown aerobically at 37° C. in Nutrient Broth (Oxoid, Basingstoke, UK) as described previously (43).

Treatment of Keratinocytes with Bacteria

Bacteria ($10^8$ CFU/ml of probiotics and $10^6$ CFU/ml of *S. aureus*) were centrifuged at 15,000×g, washed twice in 0.85% NaCl and resuspended in keratinocyte basal medium. This suspension was added directly to $5\times10^3$ cells/$cm^2$ of NHEK growing in 24 well plates. For experiments using a probiotic lysate, 10 ml of $10^8$ CFU/ml of *L. rhamnosus* GG were centrifuged, washed, resuspended in Phosphate Buffer Saline (PBS) pH=7.4 (10 mM) and lysed using a MSE Soniprep 150. Samples were filtered using a 0.22 µm pore filter (Millipore, Billerica, USA) to remove any whole bacteria remaining. Approximately 100 µl of this lysate was used to treat keratinocytes ($5\times10^3$ cells/$cm^2$). In some experiments, cells were sedimented in a centrifuge at 15,000×g for 5 minutes and the cell-free supernatant (spent culture fluid) collected and filtered using a 0.22 µm pore filter (Millipore, Billerica, USA) to remove any whole bacteria remaining. In other experiments, keratinocytes monolayers were co-infected with pathogen plus probiotics or lysates simultaneously. In separate experiments, cells were exposed to *L. rhamnosus* GG lysate 2, 4, 6, 8 and 12 hours after *S. aureus* infection had consumed. In all experiments keratinocytes were detached and cell viability was determined using trypan blue exclusion assays as described in (43).

Measurement of *S. aureus* Viability in Cell Culture

To determine whether *L. rhamnosus* GG lysates or keratinocytes were able to inhibit the growth of *S. aureus* in cell culture, keratinocytes were grown to confluence in a 24 well plate. These were exposed to *S. aureus* alone, or *S. aureus* plus *L. rhamnosus* GG lysates or conditioned medium. In separate experiments, cells were exposed to *L. rhamnosus* GG lysates 2, 4, 6, 8 and 12 hours post infection with *S. aureus*. The total number of viable staphylococci was determined by counting the colonies as described previously (43).

Measurement of Bacterial Adhesion to Keratinocytes

Confluent keratinocytes were exposed to bacteria for 1 h. Cells were then washed three times in phosphate buffered saline (PBS) pH=7.4 (10 mM) (Invitrogen, Life Technologies Ltd, Paisley, UK) to remove non adherent bacteria. The cells were trypsinised and serial dilution plate counts performed to assess the number of adherent bacteria. Selective agar was used for growth of staphylococci.

Determination of Bacterial Antagonism

A 10 µl aliquot of an overnight culture of S. aureus was inoculated into 7 ml of the soft-agar media (0.7% agar) and was added directly onto plates, pre-poured with agar base. 100 µl of each organism or extract of L. rhamnosus GG cultures were spotted onto the S. aureus lawn.

Determination of the Outcome of Co-Culture (Competition Assays)

Aliquots (100 µl) of L. rhamnosus GG lysates and S. aureus were inoculated into 10 ml WCB broths. The pH and optical density of cultures was measured at 0 and 24 h. At regular intervals (indicated in the text) bacteria were counted by serial dilution plate counts using selective agar.

Statistical Analyses

All experiments were performed a minimum of three times, with three replicates within each experiment. Data generated were analysed by one way ANOVA and post hoc Tukey test using SPSS (IBM SPSS Statistics version 16.0) program. Results were considered significant if P<0.05. Data are expressed as means±standard errors of the means (SEM).

Example 2

Results

L. rhamnosus GG Protects Keratinocytes from the Pathogenic Effects of S. aureus.

Initially, we investigated whether the viability of keratinocytes was affected by incubation with L. rhamnosus GG. However, following 24 h incubation, there was no difference in the viability of keratinocytes incubated with the probiotic bacteria vs the control of untreated keratinocytes (data not shown). Next, the ability of L. rhamnosus GG to protect keratinocytes from the effects of S. aureus was investigated. In agreement with our previous findings (43) 24 h exposure of keratinocytes to $10^6$ CFU/ml S. aureus resulted in significant keratinocyte cell death. However, keratinocytes incubated simultaneously with pathogen and L. rhamnosus GG had a significantly higher percentage viability (57% P=0.01) than monolayers infected with pathogen alone (FIG. 1).

L. rhamnosus GG Lysates and Spent Culture Fluid Protect Keratinocytes from the Effects of S. aureus.

Figure 2:
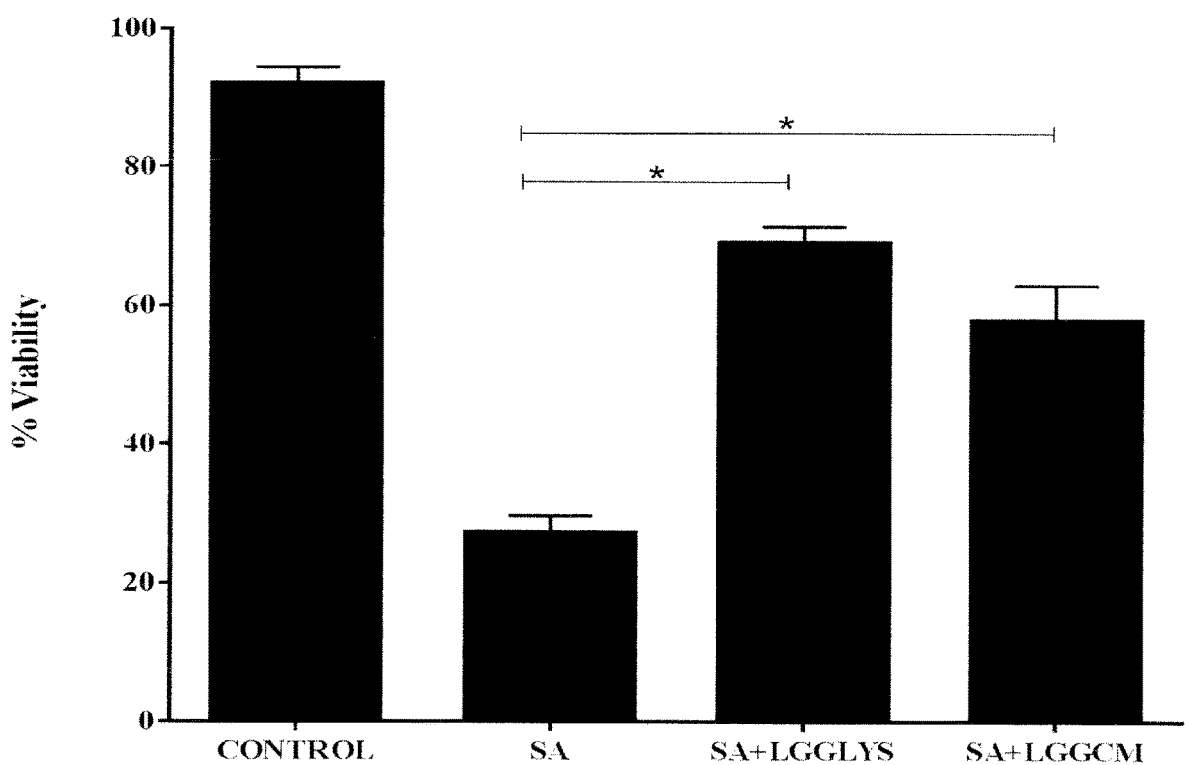
FIG. 2: Lysate and spent culture fluid (CM) from *L. rhamnosus* GG protect keratinocytes from the effects of *S. aureus*. The viability of *S. aureus* infected keratinocytes with *L. rhamnosus* GG lysate (LGGLYS+SA) was 65%±2.4 and with spent culture fluid (LGGCM+SA) was 57%±1.5 compared to 25%±3.1 in keratinocytes infected with *S. aureus* (SA) alone (P=0.006, P=0.01 respectively, n=3).

We investigated whether live bacterium was required for the protective effect of L. rhamnosus GG by examining the effect of probiotic lysate and spent culture fluid on S. aureus infected keratinocytes. Neither lysate nor spent culture fluid significantly affected the viability of keratinocytes (P>0.05) (data not shown). However, both the lysate and spent culture fluid reduced the toxicity of S. aureus such that the viability of treated keratinocytes was 65% and 57.93% respectively compared to 25% in keratinocytes infected with S. aureus alone (P=0.006 and P=0.01 respectively) (FIG. 2).

L. rhamnosus GG, Lysate but Not Spent Culture Fluid Rescues Keratinocytes from S. aureus Toxicity.

Figure 3:
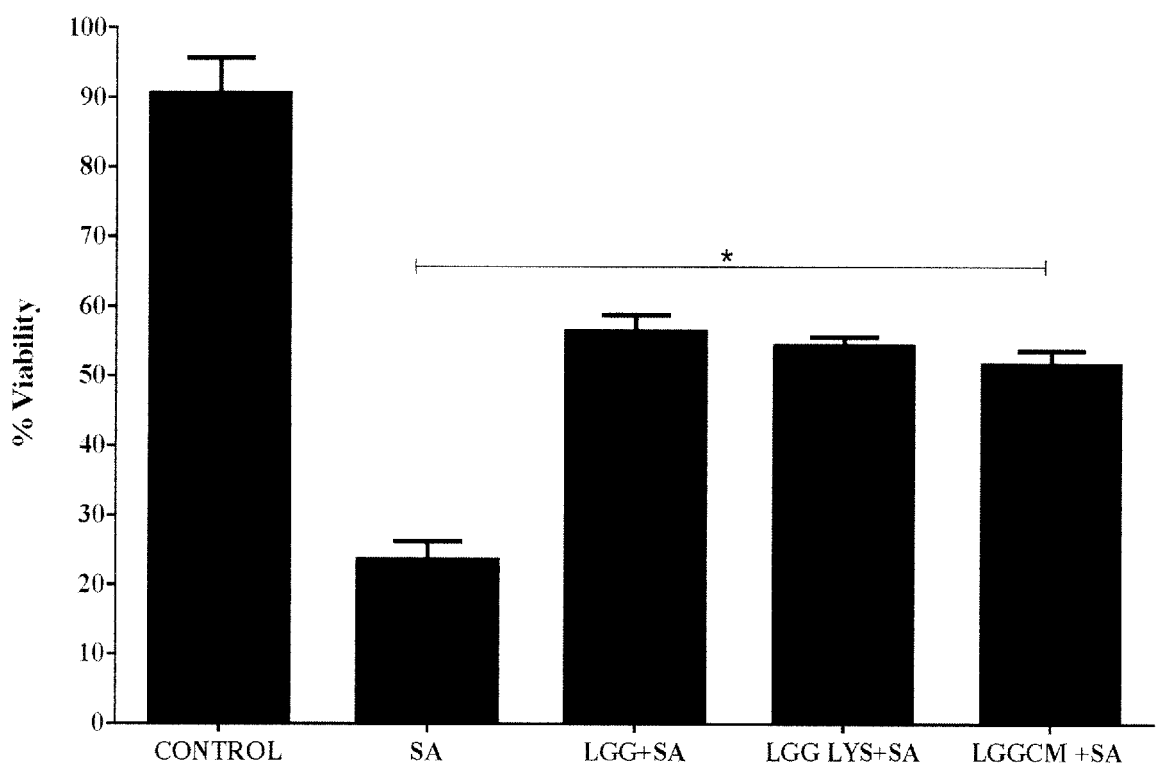
FIG. 3: *L. rhamnosus* GG protects keratinocytes from infection with *S. aureus*. Percentage viability of keratinocytes was significantly higher in cells that were pre-exposed to *L. rhamnosus* GG (LGG+SA), lysate (LGG LYS+SA) or spent culture fluid (LGG CM+SA) (58%±1.4, 57%±1.9, 55%±0.5, P=0.006, P=0.005, P=0.004) compared to *S. aureus* (SA) infected cells (25%±1.3) (n=3).
Figure 4A:
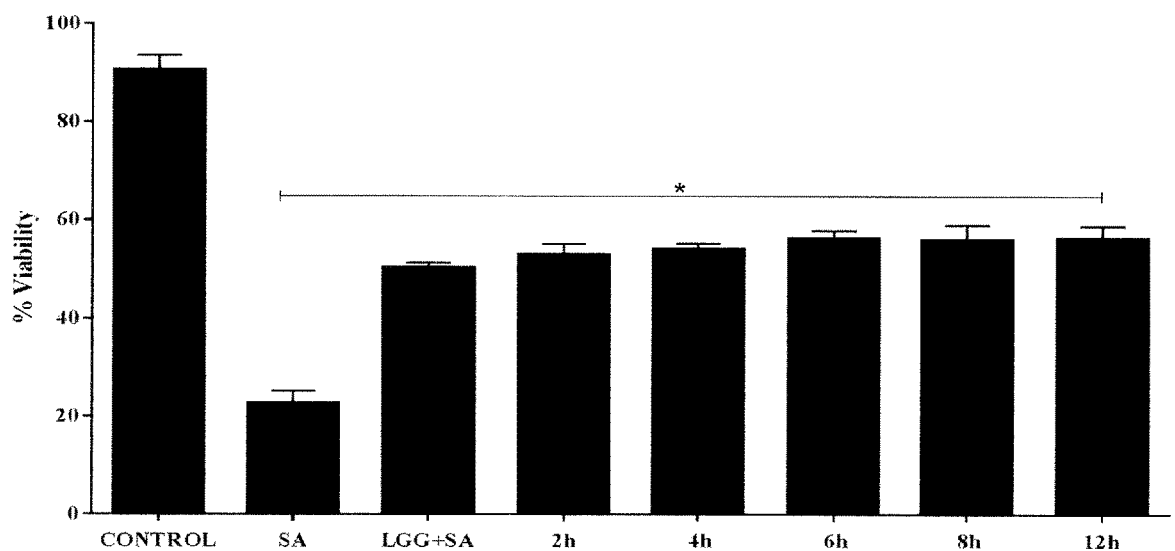
FIG. 4: *L. rhamnosus* GG but not its spent culture fluid rescuesd keratinocytes from *S. aureus* mediated toxicity. A) Uninfected keratinocytes were incubated overnight; approximately 90% of the cells were viable after 24 hours. The viability of *S. aureus* infected keratinocytes was significantly higher in cells post-exposed with *L. rhamnosus* GG (P=0.003, n=3) 2 h (52%±1.6), 4 h (54%±1.4), 6 h (57%±1.3), 8 h (58%±1.3) or 12 h (58%±1.5). B) There was significant difference between the viability of cells (P=0.01, n=3) treated with *L. rhamnosus* GG lysate 2 h (574%±3.1), 4 h (58%±2.1), 6 h (63%±1.2), 8 h (63%±1.3) or 12 h (55%±2.4) after infection had begun, whereas the viability of keratinocytes had been infected with *S. aureus* (SA) alone (25%±1.7). C) Cells post-exposed with *L. rhamnosus* GG spent culture fluid (CM) did not have significant protection (P=0.15, n=3) 2 h (32%±2.6), 4 h (39%±2.4), 6 h (37%±1.8), 8 h (36%±1.3) or 12 h (35%±3.5), whereas, the co-exposed cells had significant protection from *S. aureus* infection (56%±2.1, P=0.01, n=3).
Figure 4B:
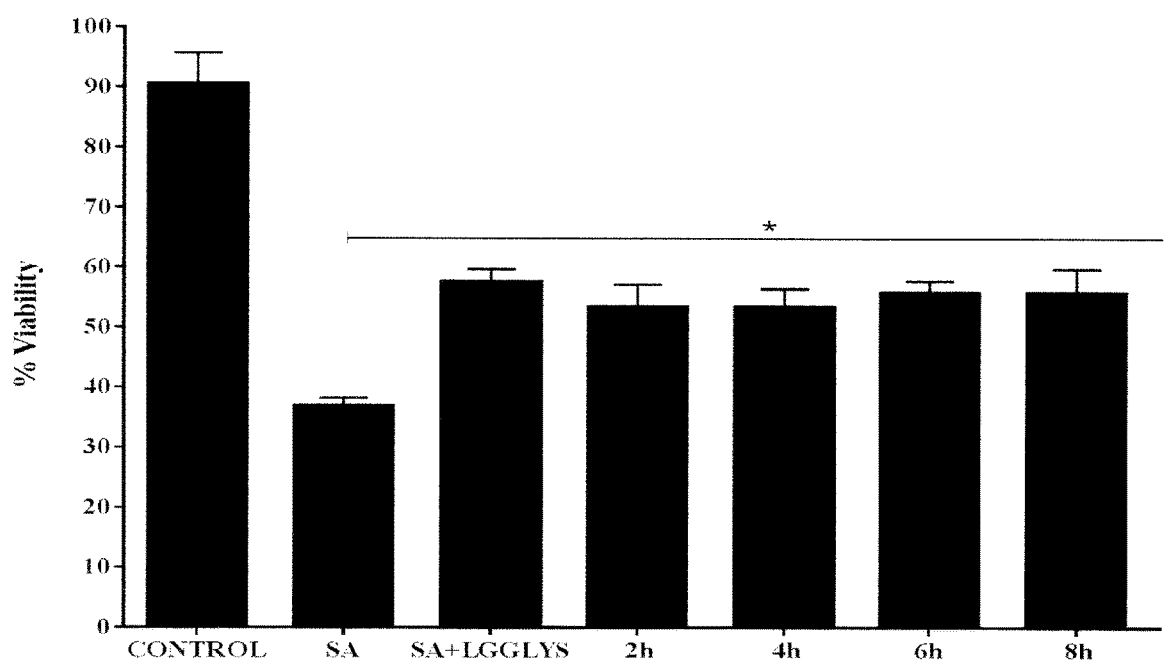
Figure 4C:
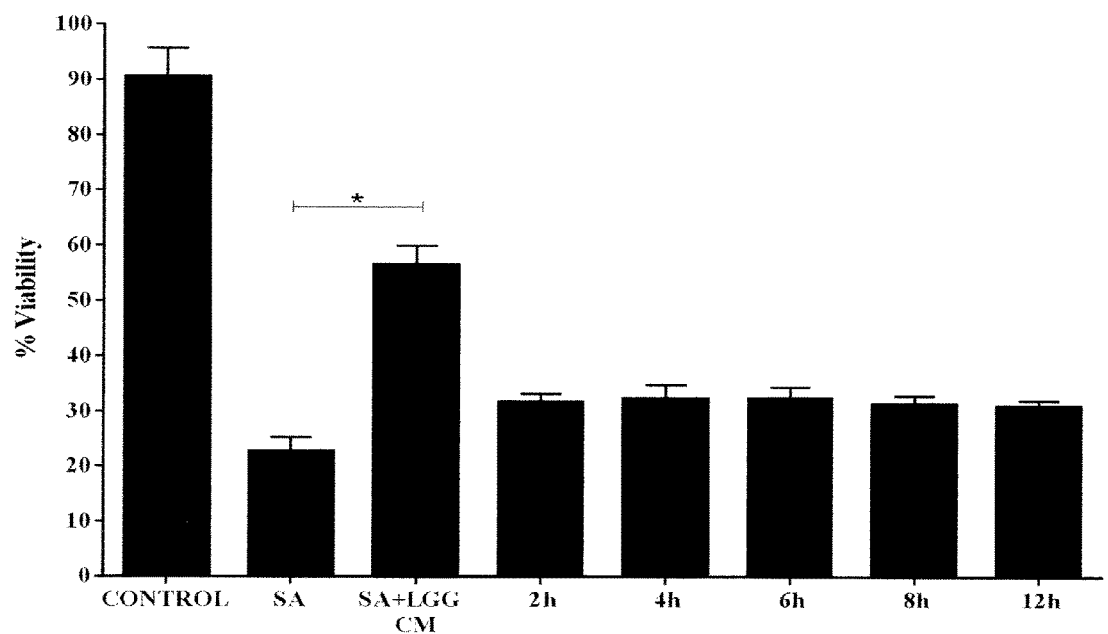

We next investigated the timing of the protective effect of L. rhamnosus GG by adding the live bacteria or the lysate either pre or post infection of keratinocytes with S. aureus. The percentage of keratinocyte viability was significantly greater in monolayers exposed to L. rhamnosus GG or spent culture fluid for 2 h prior to infection with S. aureus, than in monolayers infected with S. aureus alone (P=0.006). Both the lysate and spent culture fluid afforded a similar levels of protection (P=0.005, p=0.004), (FIG. 3). In post-infection experiment, keratinocytes were exposed to S. aureus for 2 h, 4 h, 6 h, 8 h and 12 h before addition of the live L. rhamnosus GG, lysate, or spent culture fluid. The viability of the keratinocytes was then measured at 24 h post infection with S. aureus. The data in FIG. 4 (A, B) shows that both live probiotic and its lysate could protect the keratinocytes when added after S. aureus. Even at 12 h post S. aureus infection, L. rhamnosus GG or lysate still afforded protection to the keratinocytes such that 58% and 55% respectively of cells remained viable compared to 25% when exposed to S. aureus alone (P=0.003, P=0.01 respectively). However, the spent culture fluid from L. rhamnosus GG had no protective effect on keratinocytes when added after S. aureus (FIG. 4 C).

L. rhamnosus GG Lysate, but Not Spent Culture Fluid, Inhibits the Growth of S. aureus.

Figure 5A:
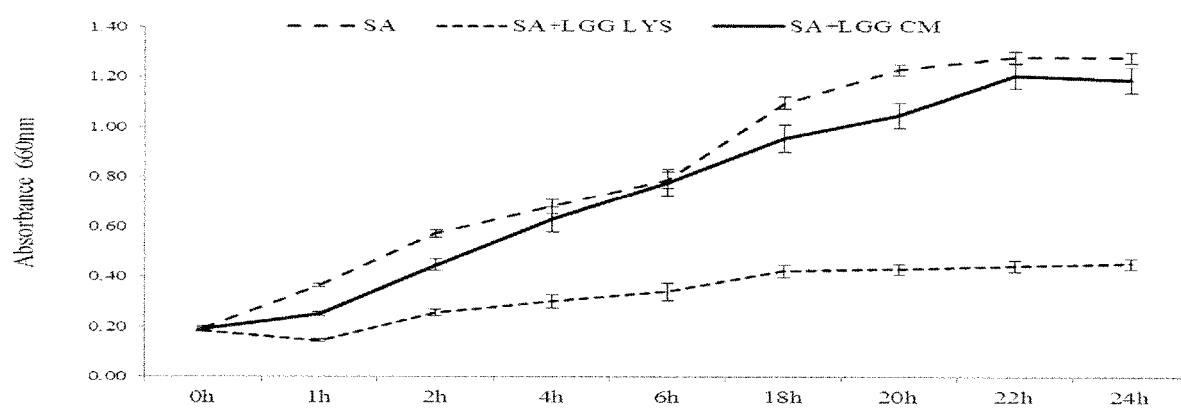
FIG. 5: *L. rhamnosus* GG lysate, but not spent culture fluid, reduced *staphylococcal* viability. A) The optical densities of cultures of *S. aureus* (SA) growing in the presence of keratinocytes and treated with *L. rhamnosus* GG lysate (LGG LYS) or spent culture fluid (LGG CM) was determined every hour to monitor the growth of the bacteria. The growth of *S. aureus* in the presence of the probiotic lysates was significantly lower than in *S. aureus* cultures (P=0.02, n=3), whereas, the spent culture fluid had no effect. B) The number of viable *S. aureus* (SA) in keratinocytes culture alone was 8 log CFU/ml or with spent culture fluid (LGG CM) 7.87 log CFU/ml, whereas 5 log CFU/ml of *S. aureus* (SA) was viable in the present of *L. rhamnosus* GG lysate. C) The total number of viable staphylococci in keratinocytes culture was reduced by the *L. rhamnosus* GG lysate in a post infection assay (2-4-6-8 and 12 hours), also showed significant reduction in *S. aureus* viability after 2 h incubation (P=0.05, n=3) compared to *S. aureus* alone.
Figure 5B:
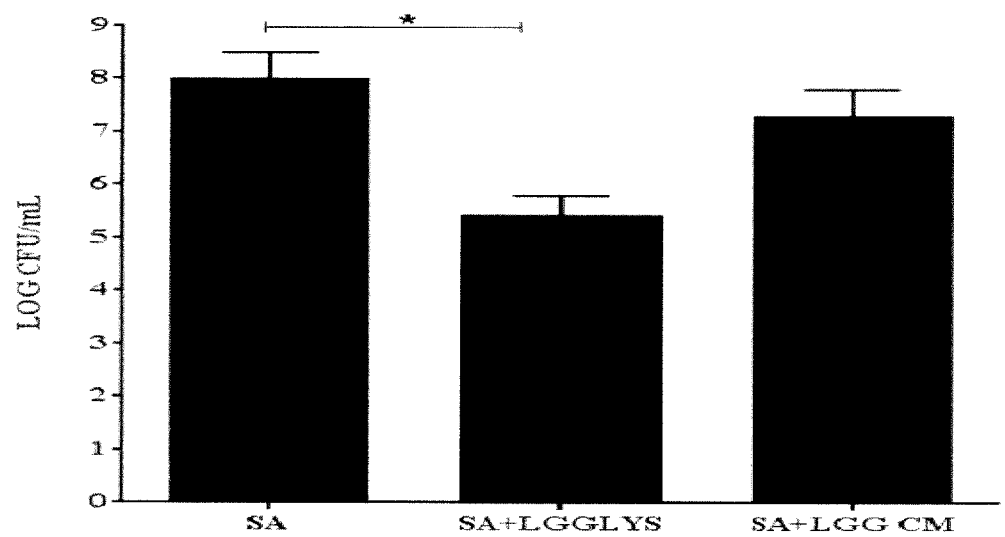
Figure 5C:
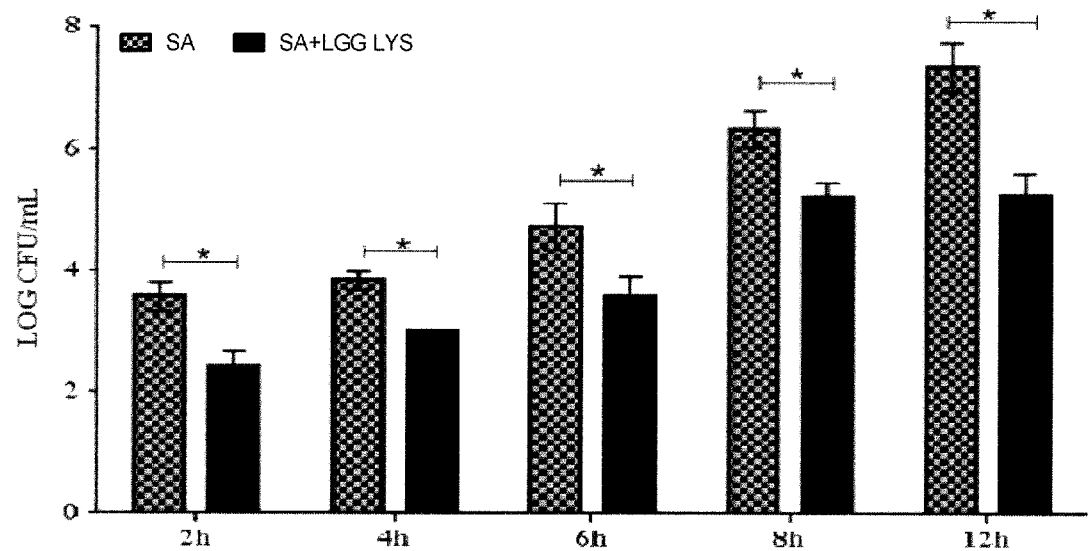

The mechanism by which the L. rhamnosus GG lysate exerted its protective effect was explored. We investigated whether the probiotic lysate had direct effects on the growth of the pathogen by growing them simultaneously in culture. Competition assays showed a significant reduction in S. aureus growth over a period of 24 h in keratinocyte culture medium in the presence of the L. rhamnosus GG lysate compared to untreated cultures (P=0.02) (FIG. 5A). However, the spent culture fluid from L. rhamnosus GG had no effect on the growth of S. aureus (FIG. 5A). The total number of viable staphylococci was also significantly reduced in the presence of the lysate (but not the spent culture fluid) to 5 $log_{10}$ cfu/ml, compared to 8 $log_{10}$ cfu/ml for S. aureus grown alone (P=0.02) (FIG. 5B). Furthermore, the total number of viable staphylococci culture was reduced with time by the L. rhamnosus GG lysate (FIG. 5C). Since Lactobacilli can produce organic acids, we measured the pH of keratinocyte media infected for 24 h with S. aureus, L. rhamnosus GG lysate or both simultaneously. However, there was no significant difference in the pH between treatments group (data not shown). We also measured the pH of lysate alone and found it be pH=7.2 thus eliminating the possibility of acid mediated effects.

L. rhamnosus GG Inhibits Adhesion of S. aureus to Keratinocytes.

Figure 6:
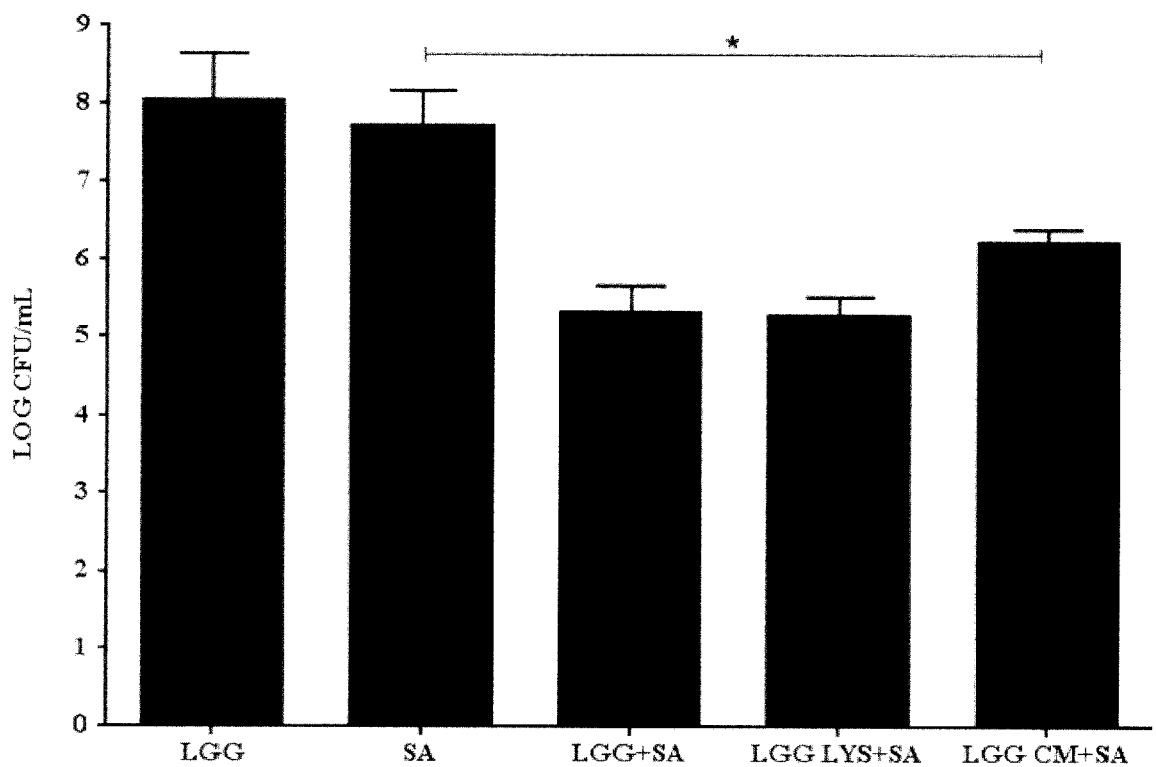
FIG. 6: Live *L. rhamnosus* GG, lysate or spent culture fluid inhibited *S. aureus* from adhering to keratinocytes by competitive exclusion from binding sites. Ability of bacteria to adhere to keratinocytes *S. aureus* (SA) ($10^6$), when applied to keratinocytes for 1 h adhered to cells at approximately 7.5±0.6 log CFU/ml, while *L. rhamnosus* GG (LGG) ($10^8$) adhered at approximately 7.9±0.5 log CFU/ml. In pre-exposed cells with *L. rhamnosus* GG (LGG+SA), lysate (LGGLYS+SA) or spent culture fluid (LGG CM+SA) had significantly less staphylococci adhered to them (5.83±0.2 log CFU/ml, 5.9±0.6 log CFU/ml and 6.4±0.7 log CFU/ml respectively) compared to cells infected with *S. aureus* (SA) alone (7.9±0.6 log CFU/ml) (P=0.04, n=3).
Figure 7:
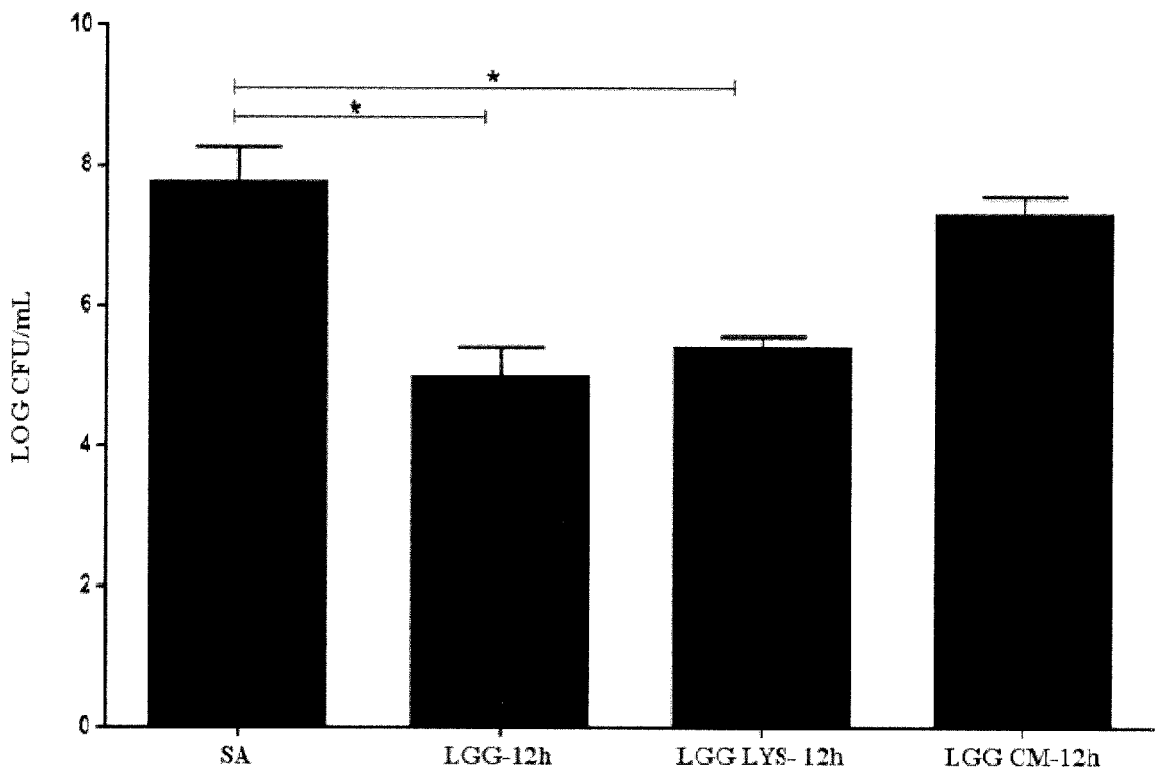
FIG. 7: Live *L. rhamnosus* GG or lysate inhibited *S. aureus* from adhering to keratinocytes by competitive displacement to binding sites. Post exposed cells with *L. rhamnosus* GG (LGG-12 h) or lysate (LGGLYS-12 h) had significantly less staphylococci adhered to them after 12 h (5.8±0.7 log CFU/ml, 5.4±0.3 log CFU/ml respectively) compared to cells infected with *S. aureus* (SA) alone (7.95±0.6 log CFU/ml) (P=0.01, n=3). Whereas, the post exposed cells with *L. rhamnosus* GG spent culture fluid (LGG CM-12 h) did not reduce the adhesion number of *S. aureus* (7±0.6 log CFU/ml, P>0.05, n=3).

Another mechanism by which live bacteria, lysate or spent culture fluid of L. rhamnosus GG may protect the keratinocytes is by inhibition of pathogenic adhesion. Previously, we showed that adhesion is a requirement for the toxic effects of S. aureus and specific probiotic such as L. reuteri protected keratinocytes by competitive exclusion of pathogen from keratinocyte binding sites (43). Hence, we considered that inhibition of adhesion also be part of the protective mechanism of L. rhamnosus GG, lysate or spent culture fluid. Adhesion assays were performed to determine whether inhibition was due to competition, exclusion or displacement of pathogen from binding sites on keratinocytes (FIG. 6 A&B and FIG. 7). Our results demonstrated that live L. rhamnosus GG or lysate were able to inhibit pathogen adhesion if keratinocytes were co-infected (competition, P=0.03), pre-exposed (exclusion, P=0.04) or even applied 12 h after infection with S. aureus had begun (displacement, P=0.01). However, the spent culture fluid only inhibited pathogen adhesion if it was added to keratinocytes either before or at the same time as the pathogen (FIG. 7).

Discussion

This study explored whether an enteric probiotic, L. rhamnosus GG could protect keratinocytes from the pathogenic effects of S. aureus. Preliminary experiments to determine the effect of adding S. aureus and L. rhamnosus GG simultaneously on keratinocyte viability indicated a significant protective effect as observed by an increase in the number of viable keratinocytes in the presence of the probiotic compared to keratinocytes infected with S. aureus alone (FIG. 1). Furthermore, the protective effect of L. rhamnosus GG did not require viable bacteria because a lysate and spent culture fluid from the probiotic also afforded protection of keratinocytes from S. aureus. The timing of application of L. rhamnosus GG or lysate did not affect the degree of protection conferred by the probiotic or lysate to protect keratinocytes against S. aureus induced cell death (FIG. 3). The data demonstrate that keratinocytes pre-, post or co-exposed to L. rhamnosus GG or lysate were protected from S. aureus induced cell death. However, the probiotic spent culture fluid only protected keratinocytes if it was added either before or at the same time as pathogen. These data suggest that there are at least two separate activities involved in the protective effects of L. rhamnosus GG against S. aureus, one contained within the spent culture fluid and one contained within the lysate.

Our data shows that the activity contained within the spent culture fluid probably has anti-adhesive effects. This is based on the following observations: A) L. rhamnosus GG-spent culture fluid only inhibits pathogen adhesion to keratinocytes if it is added before or at the same time as infection with S. aureus. B) We have shown previously that S. aureus must adhere to keratinocytes in order to be toxic to them and agents inhibiting adhesion protect keratinocytes from this pathogen (43). C) In agreement with this, spent culture fluid is only protective when added pre or co-infection with S. aureus. Other studies in vitro demonstrated that cell-free culture supernatants (CFCS) from the putative probiotics (Lactobacillus, Bifidobacterium, Lactococcus, Streptococcus) were able to inhibit the adhesion of several pathogens such as Salmonella Typhimurium, S aureus and Escherichia coli, to Caco-2 cells (11).

Keratinocyte protection by the lactobacillus lysate may involve at least two mechanisms. Firstly, the lysate may be able to reduce the growth of S. aureus. Competition assays demonstrated that L. rhamnosus GG lysate reduced the total number of viable staphylococci (FIG. 5 A, B, C). In addition, in inhibition assays, zones of inhibition were observed when S. aureus was challenged with lysates from probiotic grown anaerobically (Table 1). These data suggest an ability of L. rhamnosus GG lysate to inhibit growth of S. aureus. This could be due to the presence of a toxic molecule(s) within the probiotic that are able to directly inhibit S. aureus growth and/or viability. It is possible that this molecule(s) may be synthesized, but not secreted because there was no effect of L. rhamnosus GG spent culture fluid on the viability of S. aureus. If L. rhamnosus GG contains bacteriostatic substances, then this may also, at least partially explain the protective effect of the probiotic in keratinocyte survival assays. Probiotics, especially lactobacilli, have previously been shown to exert a strong inhibitory effect on S. aureus growth. Certain Lactobacillus strains have been reported to be highly antagonistic to biofilm-forming S. aureus (28, 30). Other studies have reported that probiotics can improve gut health by inhibiting growth of pathogens through production of bacteriocins (16, 48). Moreover, L. rhamnosus GG has been shown to inhibit the growth of Salmonella enterica through production of lactic acid (29). However, in the present study, we could find no evidence of the involvement of acid production as part of the protective effects of L. rhamnosus GG. Indeed, the lysate from this organism was neutral (pH 7.2) but was still able to inhibit S. aureus growth.

TABLE 1

Zones of Inhibition (ZOI) for S. aureus in Spot-on-the-lawn assays (n = 3). Spot on the lawn assay demonstrating zones of inhibition produced by L. rhamnosus (LGG) and lysate (LGG LYS) under anaerobic condition, but not under aerobic condition. Results are expressed as the mean ± SEM

| Organisms | (ZOI)mm |
|---|---|
| SA + LGG Anaerobic | 11 + 1.3 |
| SA + LGG Lysate Anaerobic | 18 + 0.7 |
| SA + LGG Aerobic | No inhibition |
| SA + LGG Lysate Aerobic | No inhibition |

A second mechanism by which live bacterium or lysate of L. rhamnosus GG could protect the keratinocytes is by inhibition of pathogenic adhesion. Indeed, our data demonstrated a reduction in adhesion of S. aureus to keratinocytes in the presence of L. rhamnosus GG or its lysate. This data suggests a mechanism of exclusion as we have observed previously for L. reuteri (43). However, interestingly, viable L. rhamnosus GG or its lysate also inhibited adhesion of S. aureus when added to existing infections demonstrating another mechanism of protection i.e. that L. rhamnosus GG can displace pathogen from keratinocytes (FIG. 7). Similarly, live L. rhamnosus GG has been shown to displace pathogens from the intestinal cells in the gut (47). However, our data demonstrated that the presence of live bacterium is not necessary for displacement of S. aureus from keratinocytes. Importantly, our data demonstrated species dependent differences in the mechanisms used by lactobacilli to reduce pathogen toxicity. Our previous work highlighted L. reuteri as an organism capable of excluding S. aureus form keratinocyte binding sites (43). In this study we have shown that L. rhamnosus GG can, not only, exclude pathogens but can also reduce pathogen growth and displace pathogen from keratinocytes. Of course, it is possible that this displacement activity may be related to the ability of L. rhamnosus GG to inhibit growth and further studies will be required to clarify this point.

In conclusion, we report that L. rhamnosus GG is a potential new agent to inhibit the pathogenicity of S. aureus. Furthermore, our data shows that the utility of L. rhamnosus GG on skin will not be limited by whether it can grow and survive on skin because a lysate of the organisms is just as efficacious at preventing S. aureus colonization as live bacteria. Furthermore, the lysate could be useful as prophylaxis e.g. in hand washes, but potentially as an adjunct or even an alternative to antibiotics in existing infection.

REFERENCES

1. Aly R, Shinefield H R, Litz C, Maibach H I. 1980. Role of Teichoic Acid in the Binding of Staphylococcus aureus to Nasal Epithelial Cells. J. Infect. Dis. 141:463-465.
2. Backhed F, Ley R E, Sonnenburg J L, Peterson D A, Gordon M. 2005. Host-Bacterial Mutualism in the Human Intestine. Science. 307:1915-1920.
3. Balma-Mena A, Lara-Corrales I, Zeller J, Richardson S, McGavin M J, Weinstein M. 2011. Colonization with community-acquired methicillin-resistant Staphylococcus aureus in children with atopic dermatitis: a cross-sectional study. J. Dermatol. 50:682-688.
4. Banerjee P, Merkel G, Bhunia A. 2009. Lactobacillus delbrueckii ssp. bulgaricus B-30892 can inhibit cytotoxic effects and adhesion of pathogenic Clostridium difficile to Caco-2 cells. Gut Pathogens. 1:8-16.

5. Bek-Thomsen M, Lomholt H B, Kilian M. 2008. Acne is Not Associated with Yet-Uncultured Bacteria. J. Clin. Microbiol. 46:3355-3360.
6. Borruel N, Casellas F, Antolin M, Llopis M, Carol M, Espiin E. 2003. Effects of non-pathogenic bacteria on cytokine secretion by human intestinal mucosa. J. American Gastroenterology. 98: 865-870.
7. Bowler P G, Duerden B I, Armstrong D G. 2001. Wound Microbiology and Associated Approaches to Wound Management. Clin. Microbiol. Rev. 14:244-269.
8. Burkhart C N, Burkhart C G. 2003. Microbiology's principle of biofilms as a major factor in the pathogenesis of acne vulgaris. J. Dermatol. 42:925-927.
9. Caglar E, Kavaloglu Cildir S, Ergeneli S, Sandalli N, Twetman S. 2006. Salivary mutans streptococci and lactobacilli levels after ingestion of the probiotic bacterium *Lactobacillus reuteri* ATCC 55730 by straws or tablets. Acta Odontol. Scand. 64:314-318.
10. Chen X, Xu J, Shuai J, Chen J, Zhang Z, Fang W. 2007. The S-layer proteins of *Lactobacillus crispatus* strain ZJ001 is responsible for competitive exclusion against *Escherichia coli* O157:H7 and *Salmonella typhimurium*. Int. J. Food Microbiol. 115:307-312.
11. Da bedi, Feizizadeh S, Jafarian-Dehkordi A. 2013. In vitro anti-bacterial and anti-adherence effects of *Lactobacillus delbrueckii* subsp *bulgaricus* on *Escherichia coli*. Res Pharm Sci. 4: 260-268.
12. Deepika G, Charalampopoulos D, Allen I L, Sima S, Geoffrey M G. 2010. Surface and Adhesion Properties of Lactobacilli, Adv. Appl. Microbiol. 70:127-152.
13. Di Marzio, Cinque L B, De Simone C, Cifone M G. 1999. Effect of the Lactic Acid *Bacterium Streptococcus thermophilus* on Ceramide Levels in Human Keratinocytes In Vitro and Stratum Corneum In Vivo. J. Invest. Dermatol. 113:98-106.
14. Evera Pingitore, Salvucci E, Sesma F, Nader-Macias M A. 2007. Different strategies for purification of antimicrobial peptides from Lactic Acid Bacteria (LAB). Lett. Appl. Microbiol. 46:174-180
15. Gan B S, Kim J, Reid G, Cadieux P, Howard J C. 2002. *Lactobacillus fermentum* RC-14 Inhibits *Staphylococcus aureus* Infection of Surgical Implants in Rats. J. Infect. Dis. 185:1369-1372.
16. Granato D, Perotti F, Masserey I, Rouvet M, Golliard M, Servin A, Brassart D. 1999. Cell Surface-Associated Lipoteichoic Acid Acts as an Adhesion Factor for Attachment of *Lactobacillus johnsonii* La1 to Human Enterocyte-Like Caco-2 Cells. Appl. Environ. Microbiol. 65:1071-1077.
17. Guéniche A, Bastien P, Ovigne J M, Kermici M, Courchay G, Chevalier V, Breton L. 2010. *Bifidobacterium longum* lysate, a new ingredient for reactive skin. Exp. Dermatol. 19:e1-e8.
18. Haukioja A, Tenovuo J. 2008. Probiotic bacteria affect the composition of salivary pellicle and streptococcal adhesion in vitro. Oral Microbiology and Immunology. 23: 336-343.
19. Heinemann C, Hylckama Vlieg J E T, Janssen D B, Busscher H J, Van der Mei, Reid G. 2000. Purification and characterization of a surface-binding protein from *Lactobacillus fermentum* RC-14 that inhibits adhesion of *Enterococcus faecalis* 1131. FEMS Microbiol. Lett. 190: 177-180.
20. Helgeland L, Vaage J T, Rolstad B, Midtvedt T, Brandtzaeg P. 1996. Microbial colonization influences composition and T-cell receptor V beta repertoire of intraepithelial lymphocytes in rat intestine. Immunology 89:494-501.
21. Holder I A, Boyce S T. 1994. Agar well diffusion assay testing of bacterial susceptibility to various antimicrobials in concentrations non-toxic for human cells in culture. Burns. 20:426-429.
22. Iwase T, Uehara Y, Shinji H, Tajima A, Seo H, Takada K, Agata T, Mizunoe Y. 2010. *Staphylococcus epidermidis* Esp inhibits *Staphylococcus aureus* biofilm formation and nasal colonization. Nature. 465:346-349.
23. Kintarak S, Whawell S A, Speight P M, Packer S, Nair S P. 2004. Internalization of *Staphylococcus aureus* by Human Keratinocytes. Infect. Immun. 72:5668-5675.
24. Kluytmans J, Van Belkum A, Verbrugh H. 1997. Nasal carriage of *Staphylococcus aureus*: Epidemiology, underlying mechanisms, and associated risks. Clin. Microbiol. Rev. 10:505-520.
25. Krut O, Utermohlen O, Schlossherr S, Kronke M. 2003. Strain-Specific Association of Cytotoxic Activity and Virulence of Clinical *Staphylococcus aureus* Isolates. Infect. Immun. 71:2716-2723.
26. Lai Y, Cogen A L, Radek K A, Park H J, MacLeod D T, Leichtle A, Ryan A, Di Nardo A, Gallo R L. 2010. Activation of TLR2 by a Small Molecule Produced by *Staphylococcus epidermidis* Increases Antimicrobial Defense against Bacterial Skin Infections. J. Invest. Dermatol. 130:2211-2221.
27. Lai Y, Cogen A L, Radek K A, Park H J, MacLeod D T, Leichtle A, Ryan A, Di Nardo A, Gallo R L. 2009. Commensal bacteria regulate Toll-like receptor 3-dependent inflammation after skin injury. Nat. Med. 15:1377-1382.
28. Lee Y K, Puong K Y, Ouwehand A C, Salminen S. 2003. Displacement of bacterial pathogens from mucus and Caco-2 cell surface by lactobacilli. *J. Med. Microbiol*. 52:925-930.
29. Lefteris M, Vagelis T, Domitille M, Tom A, 2006. Kinetic analysis of the antibacterial activity of probiotic lactobacilli towards *Salmonella enterica serovar Typhimurium* reveals a role for lactic acid and other inhibitory compounds. Research in Microbiology. 157: 241-247.
30. Lin M Y, Chang F J. 2000. Antioxidative Effect of Intestinal Bacteria *Bifidobacterium longum* ATCC 15708 and *Lactobacillus acidophilus* ATCC 4356. Digestive Diseases and Sciences, 45: 1617-1622.
31. Mack D R, Michail S, Wei S, McDougall L, Hollingsworth M A. 1999. Probiotics inhibit enteropathogenic *E. coli* adherence in vitro by inducing intestinal mucin gene expression. J. Physiol Gastrointest Liver Physiol. 276: G941-950
32. Maria C. Collado, Erika Isolauri, Seppo Salminen. 2008. Speci¢c probiotic strains and their combinations counteract adhesion of *Enterobacter sakazakii* to intestinal mucus. FEMS Microbiol Lett. 285: 58-64.
33. Maudsdotter L, Jonsson H, Roos S, A B Jonsson. 2011. *Lactobacilli* Reduce Cell Cytotoxicity Caused by *Streptococcus pyogenes* by Producing Lactic Acid that Degrades the Toxic Component Lipoteichoic Acid. Antimicrob. Agents Chemother. 55:1622-88.
34. Mempel M, Schmidt T, Weidinger S, Schnopp C, Foster T, Ring T, Abeck D. 1998. Role of *Staphylococcus Aureus* Surface-Associated Proteins in the Attachment to Cultured HaCaT Keratinocytes in a New Adhesion Assay. J. Invest. Dermatol. 111:452-456.

35. Mempel M, Schnopp C, Hojka H, Fesq H, Weidinger S, Schaller M, Korting H C, Ring J, Abeck D. 2002. Invasion of human keratinocytes by *Staphylococcus aureus* and intracellular bacterial persistence represent haemolysin-independent virulence mechanisms that are followed by features of necrotic and apoptotic keratinocyte cell death. Br. J. Dermatol. 146:943-951.

36. Miyoshi Y, Okada S, Uchimura T, Satoh E. 2006. A Mucus Adhesion Promoting Protein, MapA, Mediates the Adhesion of *Lactobacillus reuteri* to Caco-2 Human Intestinal Epithelial Cells. Biosci. Biotechnol. Biochem. 70:1622-1628.

37. Mbernet F, Kerneis S, Chauviere G, Fourniat J, Servin G. 1993. Inhibition of adhesion of enteroinvasive pathogens to human intestinal Caco-2 cells by *Lactobacillus acidophilus* strain LB decreases bacterial invasion. FEMS Microbiol. Lett. 110:299-306.

38. Nikawa H, Makihira S, Fukushima H, Nishimura H, Ozaki Y, Ishida K, Darmawan S, Hamada T, Hara K, Matsumoto A, Takemoto T, and Aimi R. 2004. *Lactobacillus reuteri* in bovine milk fermented decreases the oral carriage of mutans streptococci. Int. J. Food Microbiol. 95:219-223.

39. Ouwehand A C, Isolauri E, Kirjavainen P V, olkko S T, Salminen S J. 2000. The mucus binding of *Bifidobacterium lactis* Bb12 is enhanced in the presence of *Lactobacillus* GG and *Lact. delbrueckii* subsp. *bulgaricus*. Lett. Appl. Microbiol. 30:10-13.

40. Parsool N, Rampal P. 2005. *Lactobacillus casei* DN-114 001 inhibits the increase in paracellular permeability of enteropathogenic *Escherichia coli*-infected T84 cells. Research in Microbiology. 156: 256-262.

41. Peral M C, Huaman Martinez M H, Valdez C J. 2009b. Bacteriotherapy with *Lactobacillus plantarum* in burns. International Wound Journal. 6:73-81.

42. Peral M C, Rachid M M, Gobbato M N, Martinez M H, Valdez J C. 2009a. Interleukin-8 production by polymorphonuclear leukocytes from patients with chronic infected leg ulcers treated with *Lactobacillus plantarum*. Clin. Microbiol. Infect. 16:281-286.

43. Tessa P, Andrew J McBain and Catherine A O'Neill. 2012. *Lactobacillus Reuteri* Protects Epidermal Keratinocytes from *Staphylococcus Aureus* Induced Cell Death by Competitive Exclusion. Appl. Environ. Microbiol. 15:78-5119.

44. Reid G, Beuerman D, Bruce A W. 2001. Probiotic *Lactobacillus* dose required to restore and maintain a normal vaginal flora. FEMS Immunology and Medical Microbiology. 32: 37-41.

45. Rembacken B J, Snelling A M, Hawkey P M, Chalmers D M, Axon R T. 1999. Non-pathogenic *Escherichia coli* versus mesalazine for the treatment of ulcerative colitis: a randomised trial. Lancet. 354:635-639.

46. Ron E Z, Rosenberg E. 2001. Natural roles of biosurfactants. Environmental Microbiology. 3: 229-236.

47. Satu V, Matti K, Seppo S, Arthur C. Ouwehand. 2006. *Staphylococcus aureus* adheres to human intestinal mucus but can be displaced by certain lactic acid bacteria. Microbiology. 152: 1819-1826.

48. Sarika A R, Lipton A P, Aishwarya M S. 2010. Bacteriocin production by a new isolate of *Lacobacillus rhamnosus* GP1 under different culture conditions. Advance Journal of Food Science and Technology. 2: 291-297.

49. Strober W. 1997. Trypan blue exclusion test of cell viability, p. Appendix 3B. Current Protocols in Immunology. John Wiley & Sons, Inc.

50. Valdez J C, Peral M C, Rachid M, Santana M, Perdigon G. 2005. Interference of *Lactobacillus plantarum* with *Pseudomonas aeruginosa* in vitro and in infected burns: the potential use of probiotics in wound treatment. Clin. Microbiol. Infect. 11:472-479

51. Wehkamp J, Harder J, Wehkamp K, Meissner B W, Schlee V, Enders M, Sonnenborn C, Nuding U, Bengmark S, Fellermann S, Schroder K, Stange E J. 2004. NF-kB- and AP-1-Mediated Induction of Human Beta Defensin-2 in Intestinal Epithelial Cells by *Escherichia coli* Nissle 1917: a Novel Effect of a Probiotic Bacterium. Infect. Immun. 72: 5750-5758.

52. Zarate G, Nader-Macias M E. 2006. Influence of probiotic vaginal lactobacilli on in vitro adhesion of urogenital pathogens to vaginal epithelial cells. Lett Appl Microbiol. 43:174-180.

The invention claimed is:

1. A topical composition comprising emulsion stabilizer and a culture medium from a culture of probiotic bacterium, said probiotic bacterium consisting essentially of *Lactobacillus rhamnosus, L. rhamnosus* GG, or a combination thereof, said topical composition having anti-microbial activity and being essentially free of intact probiotic bacteria, lysed probiotic bacteria, and probiotic bacterial fragments.

2. The topical composition according to claim 1 comprising a dermal penetration enhancer.

3. The topical composition according to claim 1 wherein the probiotic bacterium consist essentially of *Lactobacillus rhamnosus* bacteria.

4. The topical composition according to claim 1 wherein the probiotic bacterium consists essentially of *Lactobacillus rhamnosus* and *L. rhamnosus* GG.

5. The topical composition according to claim 1 comprising a preservative.

6. The topical composition according to claim 1 wherein the composition is a cream, gel, paste, ointment, lotion, oil, foam, suspension, emulsion, a powder or spray.

7. The topical composition according to claim 1 wherein the *Lactobacillus rhamnosus, L. rhamnosus* GG, or a combination thereof are cultured in the culture medium under anaerobic conditions.

8. A pharmaceutical composition comprising the topical composition of claim 1.

9. The topical composition according to claim 1, wherein the composition is a medicament.

10. The topical composition according to claim 9 wherein the medicament is a bacterial infection or a skin infection medicament.

11. The topical-composition according to claim 9 wherein the medicament is an anti-*Staphylococcus* or anti-*S. aureus* medicament.

12. The topical composition according to claim 9 wherein the medicament is an anti-skin infection medicament.

13. A method of preventing a bacterial infection comprising administering the topical composition of claim 1.

14. The method of preventing an infection according to claim 13 wherein the infection is a *Staphylococcal infection* or a *S. aureus* infection.

15. The method of preventing a bacterial infection according to claim 13 wherein the infection is a skin infection.

16. The method of preventing a bacterial infection according to claim 13, wherein the treatment comprises administering the topical composition to skin.

17. The topical composition of claim 1 comprising a permeation enhancer, an adsorption enhancer, or a combination thereof.

18. The topical composition of claim 1 comprising an adjuvant, an excipient, a diluent, a filler, a buffer, an antioxidant, a lubricant, a stabilizer, a solubilizer, a surfactant, a masking agent, a colouring agent, a flavouring agent, a sweetening agent, or any combination thereof.

19. The topical composition of claim 1 comprising a liposomal preparation.

20. A topical composition comprising a dermal penetration enhancer and a culture medium of a culture of probiotic bacterium consisting essentially of *Lactobacillus rhamnosus, L. rhamnosus* GG, or a combination thereof, said topical composition having anti-microbial activity and being essentially free of intact probiotic bacteria, lysed probiotic bacteria, and probiotic bacterial fragments.

* * * * *